US008809571B2

(12) United States Patent
Sedelmeier

(10) Patent No.: US 8,809,571 B2
(45) Date of Patent: Aug. 19, 2014

(54) PROCESS FOR THE PRODUCTION OF 2-AMINO-2-[2-(4-$C_{2-20}$-ALKYL-PHENYL) ETHYL]PROPANE-1,3-DIOLS, AND TO COMPOUNDS FOR USE THEREIN

(75) Inventor: Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 329 days.

(21) Appl. No.: 12/933,131

(22) PCT Filed: Mar. 17, 2009

(86) PCT No.: PCT/EP2009/053163
§ 371 (c)(1),
(2), (4) Date: Sep. 17, 2010

(87) PCT Pub. No.: WO2009/115534
PCT Pub. Date: Sep. 24, 2009

(65) Prior Publication Data
US 2011/0015425 A1    Jan. 20, 2011

(30) Foreign Application Priority Data
Mar. 19, 2008   (EP) .................................... 08153033

(51) Int. Cl.
*C07C 229/00*    (2006.01)
(52) U.S. Cl.
USPC ........................................................ 560/39
(58) Field of Classification Search
USPC ........................................................ 560/39
See application file for complete search history.

(56) References Cited

U.S. PATENT DOCUMENTS

2002/0072635 A1   6/2002  Abel et al.
2008/0249070 A1*  10/2008 Lynch et al. ................. 514/114

FOREIGN PATENT DOCUMENTS

| CN | 1380279 A | 11/2002 |
|---|---|---|
| JP | 2002-529441 A | 9/2002 |
| WO | 94/08943 A1 | 4/1994 |
| WO | WO 95/03271 | * 2/1995 |
| WO | WO 00/27798 | * 5/2000 |
| WO | 0053569 | 9/2000 |
| WO | 2006129688 A1 | 12/2006 |

OTHER PUBLICATIONS

Abstact Friedrich Marko et al, Synlett 2002, No. 4, 619-621.
Friedrich et al., "Extending the Scope of a Known Furan Synthesis—A Novel Route to 1,2,4-Trisubstituted Pyrroles", Synlett No. 4, pp. 619-621, 2002.
Pellicciara et al., "Modulation of the Kynurenine Pathway in search for New Neuroprotective Agents. Synthesis and Preliminary Evaluation of (m-Nitrobenzoyl)alanine, a potent Inhibitor of Kynurenine-3-hydroxylase", Journal of Medicinal Chemistry, 37(5) pp. 647-655 (1994).
Chemical Abstracts, Pellicciara et al., Modulaters of the kynurenine pathway of tryptophan metabolism: synthesis and preliminary biological evaluation of (S)-4-(ethylsulfonyl)benzoylalanine, a potent and selective kynurenine aminotransferase II (KAT II) inhibitor, XP002537424, Database accession No. 2006:519295 [Chemmedchem, vol. 1(5), pp. 528-531, (2006)].
Chemical Abstracts, Friedrich et al., "Extending the scope of a known furan synthesis—a novel route to 1, 2, 4-trisubstituted pyrroles", XP002537425, Database accession No. 2002:295910 [Synlett. vol. 4. pp. 619-621. (2002)].
Durand et al. "A new efficient synthesis of the immunosuppressive Agent FTY-720" Synthesis 2000, No. 4, pp. 505-506, 2000.

* cited by examiner

*Primary Examiner* — Brandon Fetterolf
*Assistant Examiner* — Blaine G Doletski
(74) *Attorney, Agent, or Firm* — Andrew Holmes

(57) ABSTRACT

The present invention relates to improved processes for the production of 2-amino-2-[2-(4-$C_{2-20}$-alkyl-phenyl)ethyl] propane-1,3-diols, and to compounds for use therein.

9 Claims, No Drawings

PROCESS FOR THE PRODUCTION OF 2-AMINO-2-[2-(4-C$_{2-20}$-ALKYL-PHENYL)ETHYL] PROPANE-1,3-DIOLS, AND TO COMPOUNDS FOR USE THEREIN

This application is a 371 of PCT/EP2009/053163 filed on Mar. 17, 2009, which claims benefit of EP application No. 08153033.9 Filed on Mar. 19, 2008, which in their entiret are herein incorporated by reference.

The present invention relates to processes for the production of 2-amino-2-[2-(4-C$_{2-20}$-alkyl-phenyl)ethyl]propane-1,3-diols, and to compounds for use therein.

2-Amino-2-[2-(4-C$_{2-20}$-alkyl-phenyl)ethyl]propane-1,3-diols are disclosed in EP-A-1627406 the relevant disclosure of which is incorporated herein by reference. On the basis of observed activity, the compounds have been found to be useful as immunosuppressants. Accordingly, the compounds may be useful in the treatment or prevention of acute allograft rejection, autoimmune diseases or xenograft rejection. A particular compound of this type is FTY720, i.e. 2-amino-2-[2-(4-octylphenyl)ethyl]propane-1,3-diol, which has the following structure:

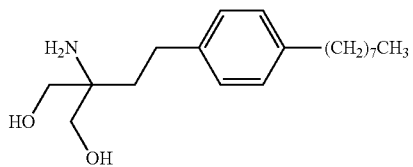

FTY720 has been found to be useful in the prevention of autoimmune diseases, such as multiple sclerosis. FTY720 is the first-in-class sphingosine 1-phosphate (SIP) receptor modulator which has been effective in clinical trials for Multiple Sclerosis.

WO 00/27798 discloses various processes for the preparation of 2-amino-2-[2-(4-C$_{2-20}$-alkyl-phenyl)ethyl]propane-1,3-diols. Some of these processes are illustrated in the reaction scheme below in relation to the production of FTY720, using the reference numerals given in the publication:

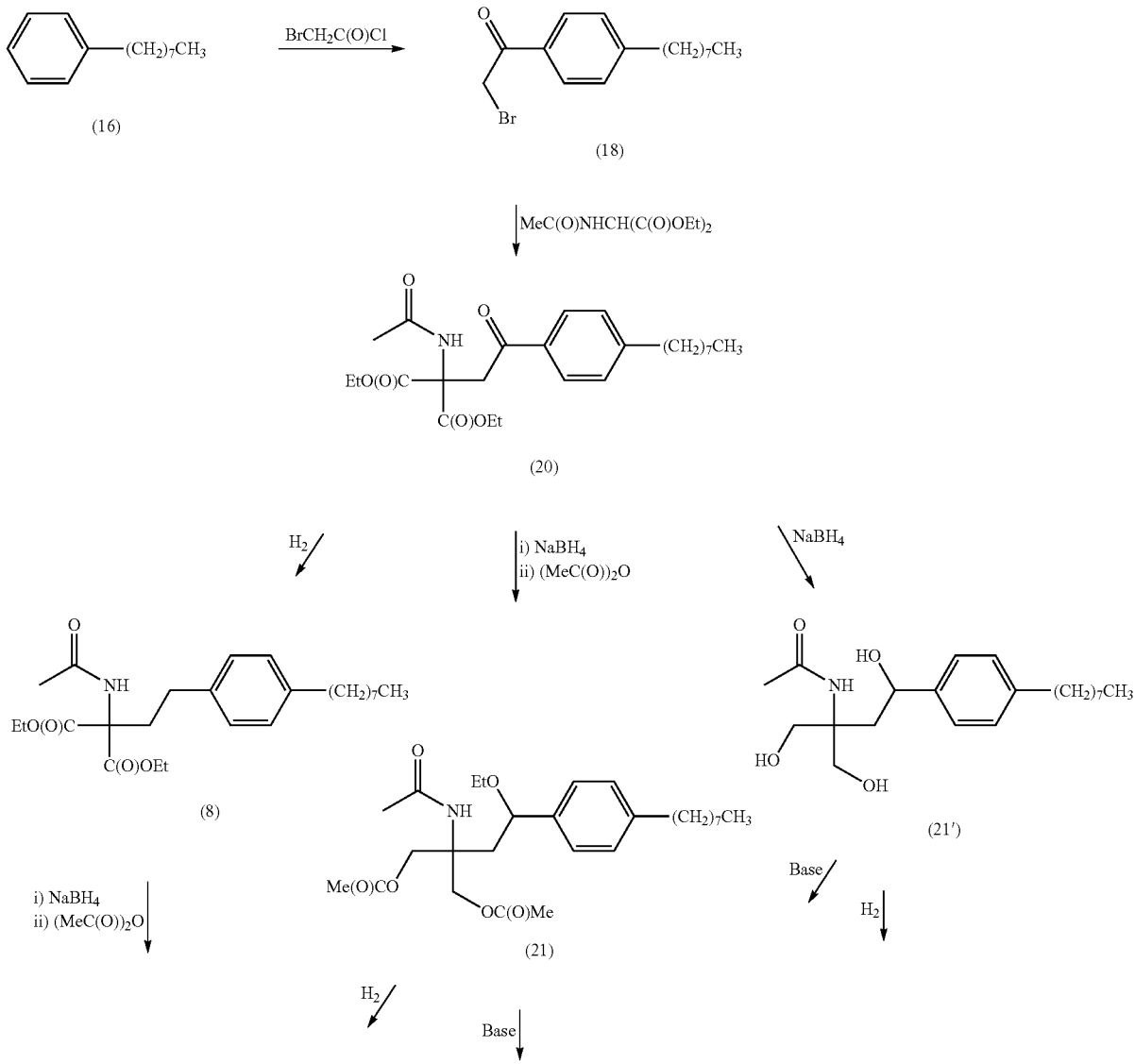

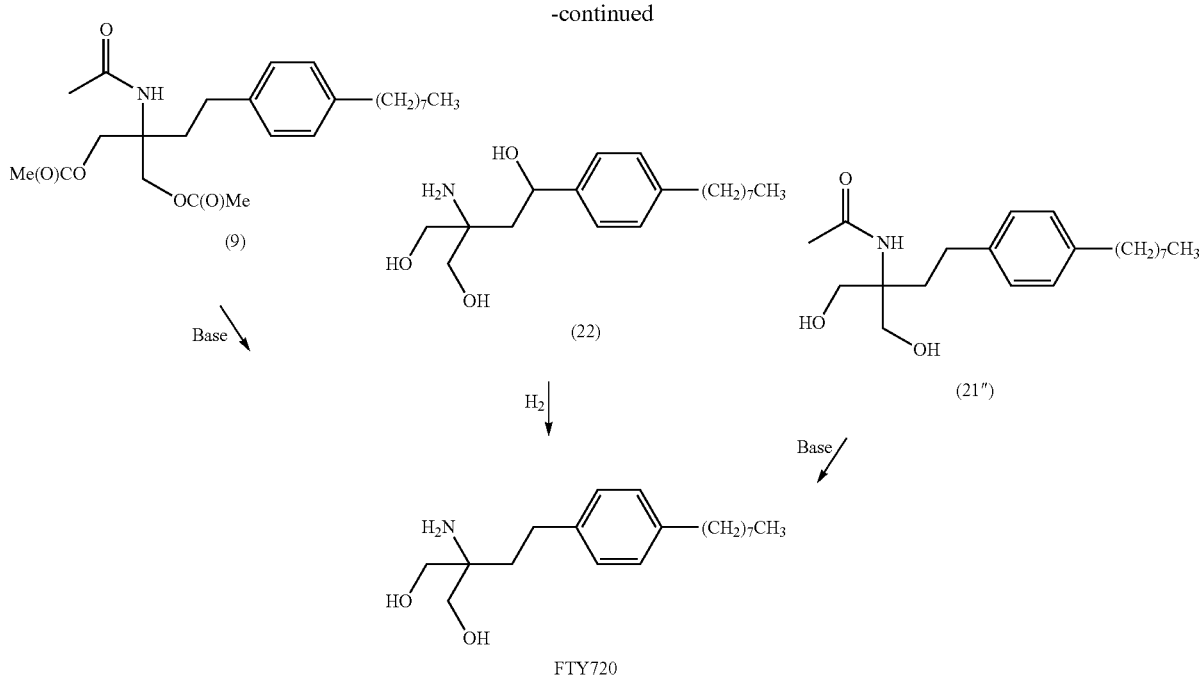

The above processes involve formation of intermediate 18 via acylation of compound 16. However, the acylation process results in a mixture of ortho-, meta- and para-substituted products. None all these products have biological activity. There is a need for a processes for producing 2-amino-2-[2-(4-$C_{2-20}$-alkyl-phenyl)ethyl]propane-1,3-diols, in particular FTY720 and salts thereof, which have improved regioselectivity for the para-position of the benzene ring.

Furthermore the above processes involve many steps, i.e. many purifications or separations of the intermediates between each steps, either e.g. by crystallization, extraction filtration and/or precipitation. There is a need for an improved production route requiring less intermediate purifications or working-up.

In accordance with the present invention, novel processes for the production of 2-amino-2-[2-(4-$C_{2-20}$-alkyl-phenyl) ethyl]propane-1,3-diols, in particular FTY720, in free form or in salt form, are provided.

The novel processes of the invention can be performed on a continuous flow mode, e.g. as a multi-component cascade reaction. For example free form of FTY720 could build up in a continuous way, e.g. in only one step. This improved method may reduce or even eliminate the need of purifying or separating the different intermediates. The process of the invention may reduce or even eliminate the purifications and separations between the steps.

The present invention provides processes for the production of 2-amino-2-[2-(4-$C_{2-20}$-alkyl-phenyl)ethyl]propane-1,3-diols, in particular FTY720, in free form or in salt form, on a continuous flow, e.g. a multi-component Domino reaction.

Multi-component cascade reaction (or multi-component Domino reactions) are defined as sequences of uni- or bi-molecular elementary reactions that proceed without intermediate isolation or workup on the compounds formed in the previous step(s). According to the invention, the reagents may be added in a well-defined sequential order, with or without modifying the conditions between adding them. In another embodiment, the reagents are all present from the beginning of the process, and the conditions are changed sequentially. Multi-component Domino reactions are known in the art, and are described e.g. in "Domino Reactions in Organic Synthesis", Angew. Chem. Int. Ed. Vol. 46, 17 Pages: 2977-2978.

In a first aspect, there is provided a process for the production of a compound of the Formula (I), e.g. FTY720, or a pharmaceutically acceptable salt thereof:

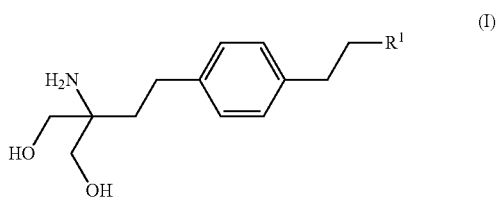

wherein $R^1$ is hydrogen or $C_{1-18}$ alkyl;
which comprises:
(a) reducing a compound of the Formula (III):

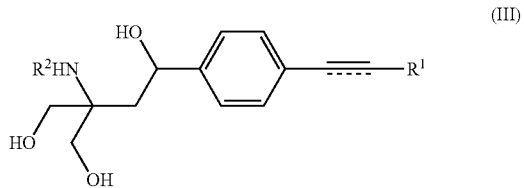

wherein $R^2$ is a protecting group; and "----" represents an optional third bond;

to form a compound of the Formula (II):

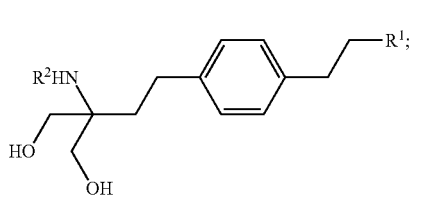

(b) deprotecting the compound of Formula (I a compound of Formula (I); and
(c) optionally converting the compound of Formula (I) to a pharmaceutically acceptable salt.

Reduction of the compound of Formula (III) to a compound of Formula (II) may be accomplished by hydrogenation, e.g. in the presence of a catalyst such as a Pd—C catalyst.

A compound of Formula (III) may be obtained by reacting a compound of the Formula (V):

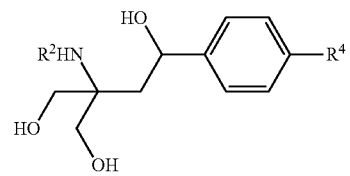

wherein $R^4$ is a leaving group;

with a compound of the Formula (VI):

Coupling of the compounds of Formulae (V) and (VI) may be achieved using processes known in the art, e.g. metal-catalysed coupling reactions. Of particular mention is the Sonogashira coupling (see, for example, Synthesis (5), 761, (2007); Catalysis Communications, 7, 377 (2006); Org. Synth. Coll., 9, 117 (1998); Tet. Lett., 50, 4467 (1975); J.O.C. 63, 8551 (1998); Djakovitch et al., Adv. Synth. Catal. 346, 1782-1792 (2004); or Hua et al., Journ. Org. Chem., 71, 2535 (2006)). Thus, in a particular embodiment, reaction of the compounds of Formulae (V) and (VI) is performed in the presence of a palladium catalyst. One or both of a copper co-catalyst and an amine may also be present. By way of example, the palladium catalyst may comprise one or more ligands selected from halo (e.g. chloro) and phosphine (e.g. triphenylphosphine) ligands. The copper co-catalyst may be, for example, a copper halide, e.g. copper iodide. The amine may be, for example, triethylamine.

A compound of Formula (V) may be obtained by reducing a compound of the Formula (VII):

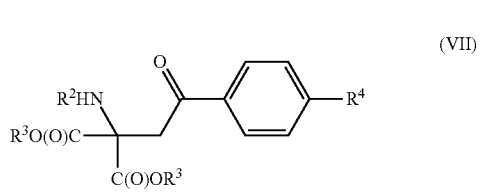

wherein each $R^3$ is independently $C_{1-4}$ alkyl.

By way of example, reduction of the compound of Formula (VII) may be accomplished using a reducing agent such as an alkali metal borohydride. Of particular mention is sodium borohydride.

A compound of Formula (VII) may be obtained by reacting a compound of the Formula (VIII):

with a compound of the Formula (IX):

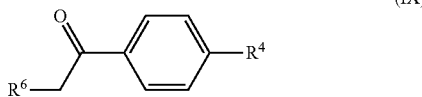

wherein $R^6$ is a leaving group.

Reaction of the compounds of Formulae (VIII) and (IX) is typically performed in the presence of a base capable of abstracting the proton from the carbon atom located α- to the nitrogen atom of the compound of Formula (VIII). Exemplary bases include sodium ethanolate (sodium ethoxide).

A compound of Formula (III) may also be obtained by reducing a compound of the Formula (X):

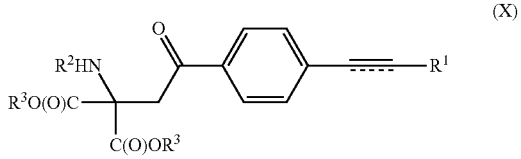

wherein each $R^3$ is independently $C_{1-4}$ alkyl.

By way of example, reduction of the compound of Formula (X) may be accomplished using a reducing agent such as an alkali metal borohydride. Of particular mention is sodium borohydride.

A compound of Formula (X) may be obtained by reacting a compound of the Formula (VII):

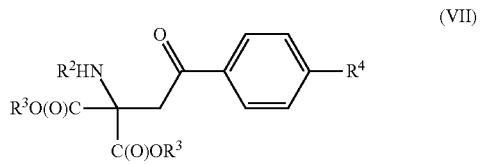

with a compound of the Formula (VI):

(VI)

Coupling of the compounds of Formulae (VII) and (VI) may be achieved using processes known in the art, e.g. Sonogashira coupling and other metal-catalysed coupling reactions. In a particular embodiment, reaction of the compounds of Formulae (VII) and (VI) is performed in the presence of a palladium catalyst, a copper co-catalyst and an amine. By way of example, the palladium catalyst may comprise one or more ligands selected from halo (e.g. chloro) and phosphine (e.g. triphenylphosphine) ligands. The copper co-catalyst may be, for example, a copper halide, e.g. copper iodide.

A compound of Formula (X) may also be obtained directly by reacting compounds of the Formulae (VIII), (IX) and (VI), on a continuous flow, e.g. as a multi-component Domino reaction. Optionally in a first step the compounds of the Formulae (VIII) and (IX) are mixed (leading to the formation of a compound of formula (VII), and in a consecutive step, a compound of formula (VI) is added, leading to the formation of the compound of Formula (X).

The present invention also provides an alternative process for the production of a compound of the Formula (I), e.g. FTY720, or a pharmaceutically acceptable salt, which comprises:
(a) reducing a compound of the Formula (X) to form a compound of the Formula (IV) (as hereinbelow described);
(b) reducing the compound of Formula (IV) to form a compound of Formula (II);
(c) deprotecting the compound of Formula (II) to form a compound of Formula (I); and
(d) optionally converting the compound of Formula (I) to a pharmaceutically acceptable salt.

By way of example, reduction of the compound of Formula (X) to a compound of Formula (IV) may be achieved by hydrogenation, e.g. in the presence of a catalyst such as a Pd—C catalyst. Reduction of the compound of Formula (IV) may be accomplished using a reducing agent such as an alkali metal borohydride. Of particular mention is sodium borohydride.

In another embodiment, a compound of Formula (II) may be produced on a continuous flow process, e.g. through a domino reaction, directly from a compound of Formula (X), wherein the process comprises the steps of:
(a) reducing a compound of Formula (X) to form a compound of Formula (IV); and
(b) reducing the compound obtained in step (a) to form a compound of Formula (II).

The reductions in steps (a) and (b) can be performed as hereinabove described.

In a further process, a compound of Formula (X) is reduced to a compound of Formula (III).

Thus, the invention also provides a process for the production of a compound of Formula (I), e.g. FTY720, or a pharmaceutically acceptable salt thereof, which comprises:
(a) reducing a compound of the Formula (X) to form a compound of the Formula (III):
(b) reducing the compound of Formula (III) to form a compound of Formula (II);
(c) deprotecting the compound of Formula (II) to form a compound of Formula (I); and
(c) optionally converting the compound of Formula (I) to a pharmaceutically acceptable salt, wherein the process is optionally performed on a continuous flow, e.g. as a domino reaction.

In another process, a compound of Formula (X) is reduced directly to a compound of Formula (II). Thus, the invention also provides a process for the production of a compound of Formula (I), e.g. FTY720, or a pharmaceutically acceptable salt thereof, which comprises:
(a) reducing a compound of the Formula (X) to form a compound of the Formula (II);
(b) deprotecting the compound of Formula (II) to form a compound of Formula (I); and
(c) optionally converting the compound of Formula (I) to a pharmaceutically acceptable salt,
wherein the process is optionally performed on a continuous flow, e.g. as a domino reaction.

Reduction of the compound of Formula (X) to a compound of Formula (II) may be achieved by, for example, hydrogenation, typically in the presence of a catalyst such as Pd—C. In a particular embodiment, the compound of Formula (X) is reduced by hydrogenation in the presence of a protic, acidic solvent such as acetic acid. Suitable procedures are known to those skilled in the art.

In yet another process, a compound of Formula (X) is produced on a continuous flow, e.g. as a domino reaction. For example the compound of Formula (X) is produced directly from a mixture of a compound of Formula (VIII), a compound of Formula (IX) and a compound of Formula (VI), i.e. without working up, e.g. without purifying, the intermediate compound of Formula (VII). The compounds of Formulae (VIII), (IX) and (VI) can be mixed from the beginning of the reaction. Alternatively, the compounds of Formulae (VIII) and (IX) can be mixed first, and only after a compound of Formula (VI) will be added. The coupling of the compounds of Formulae (VIII) and (IX) may be performed as hereinabove described. The coupling of the compounds of Formulae (VII) and (VI) may also be performed as hereinabove described, e.g. through Sonogashira process.

Thus, the invention also provides a process for the production of a compound of Formula (X), which comprises:
(a) reacting compounds of the Formulae (VIII) and (IX) to obtain a compound of Formula (VII):
(b) reacting a compound of the Formula (VI) directly to the compound obtained in step (a) to obtain a compound of Formula (X)
wherein the process is performed on a continuous flow, e.g. as a domino reaction.

Thus, the invention also provides a continuous process, e.g. a multi-component domino reaction, for the production of a compound of Formula (I), e.g. FTY720, or a pharmaceutically acceptable salt thereof, which comprises
(a) reacting compounds of the Formulae (VIII) and (X) to obtain a compound of Formula (VII);
(b) reacting a compound of the Formula (VI) directly to the compound obtained in step (a) to obtain a compound of Formula (X);
(c) reducing the compound directly obtained in step (b) to obtain a compound of Formula (II);
(d) deprotecting the compound of Formula (II) to form a compound of Formula (I); and
(e) optionally converting the compound of Formula (I) to a pharmaceutically acceptable salt.
Optionally the step (c) is performed as follows:
(c1) reducing the compound directly obtained in step (b) to obtain a compound of Formula (IV); and
(c2) reducing the compound directly obtained in step (c1) to obtain a compound of Formula (II).

For the purposes of illustration only, the following reaction scheme summarises various processes of the invention:
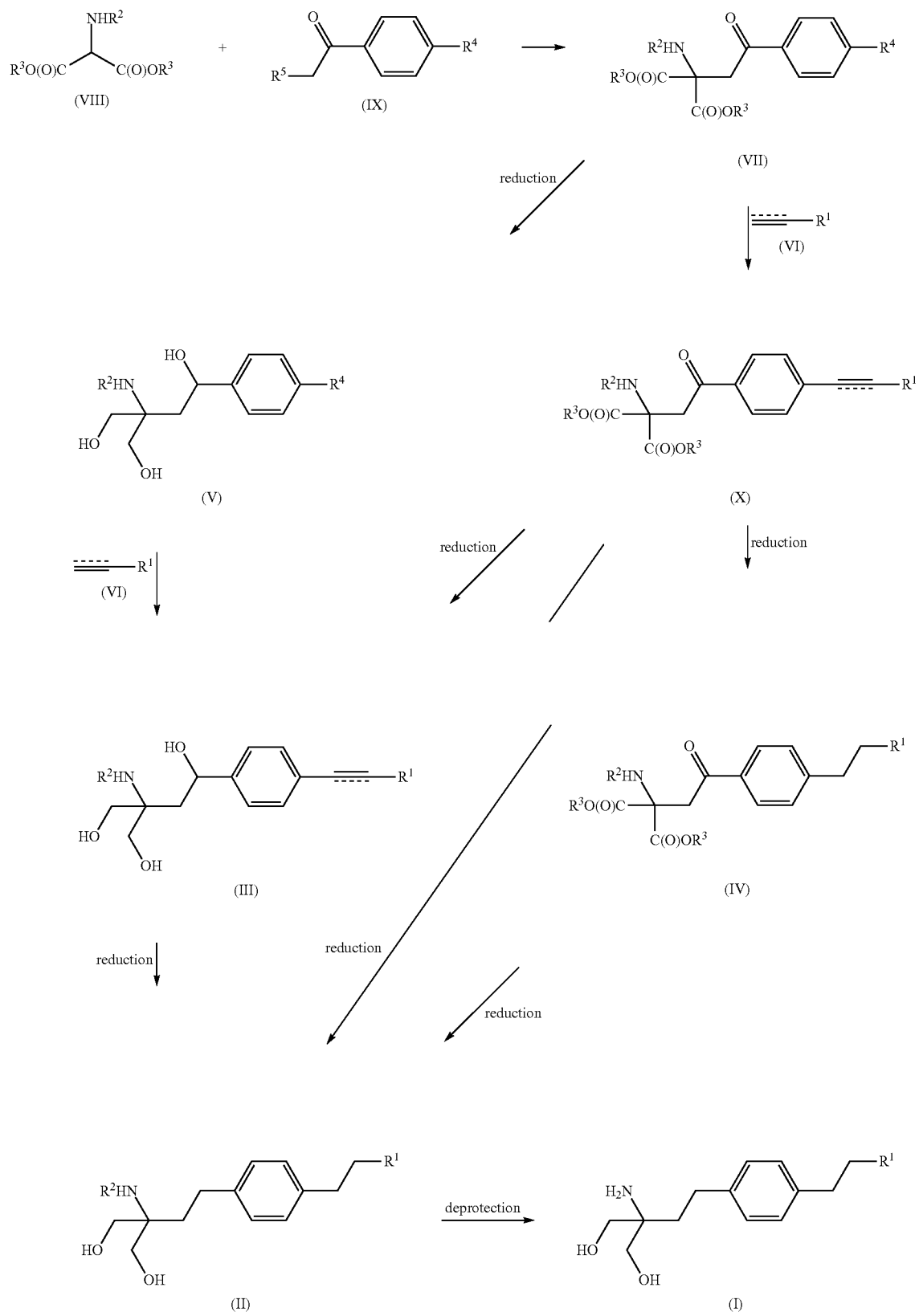

As can be seen from the Scheme above, the use of compounds of Formula (IX), which are readily available from commercial sources, provides for a regioselective process in which formation of para-substituted products is controlled.

The invention includes the above processes for making the compound of Formula (I), as well as each step thereof and all combinations of sequential steps. As mentioned above, the compound of Formula (I), e.g. FTY720, may further be converted to a pharmaceutically acceptable salt form.

Particular processes are set out in the numbered paragraphs below:

1. A process for the production of a compound of the Formula (I) or a pharmaceutically acceptable salt thereof, which comprises:
   (a) reducing a compound of the Formula (III) to form a compound of the Formula
   (b) deprotecting the compound of Formula (II) to form a compound of Formula (I); and
   (c) optionally converting the compound of Formula (I) to a pharmaceutically acceptable salt.
2. A process according to paragraph 1, wherein the compound of Formula (III) is obtained by reacting a compound of the Formula (V) with a compound of the Formula (VI).
3. A process according to paragraph 2, wherein the compound of Formula (V) is obtained by reducing a compound of the Formula (VII).
4. A process according to paragraph 3, wherein the compound of Formula (VII) is obtained by reacting a compound of the Formula (VIII) with a compound of the Formula (IX).
5. A process according to paragraph 1, wherein the compound of Formula (III) is obtained by reducing a compound of the Formula (X).
6. A process according to paragraph 5, wherein the compound of Formula (X) is obtained by reacting a compound of the Formula (VII) with a compound of the Formula (VI).
7. A process according to paragraph 6, wherein the compound of Formula (VII) is obtained by reacting compounds of the Formulae (VIII) and (IX) according to paragraph 4.
8. A process according to paragraph 5, wherein the compound of Formula (X) is obtained by reacting compounds of the Formulae (VIII), (IX) and (VI).
9. A process for the production of a compound of the Formula (I) or a pharmaceutically acceptable salt thereof, which comprises:
   (a) reducing a compound of the Formula (X) to form a compound of the Formula (IV);
   (b) reducing the compound of Formula (IV) to form a compound of the Formula (II);
   (c) deprotecting the compound of Formula (II) to for a compound of Formula (I); and
   (d) optionally converting the compound of Formula (I) to a pharmaceutically acceptable salt.
10. A process for the production of a compound of the Formula (I) or a pharmaceutically acceptable salt thereof, which comprises:
    (a) reducing a compound of the Formula (X) to form a compound of the Formula (II);
    (b) deprotecting the compound of Formula (II) to form a compound of Formula (I); and
    (c) optionally converting the compound of Formula (I) to a pharmaceutically acceptable salt.
11. A process for the production of a compound of the Formula (I) or a pharmaceutically acceptable salt thereof, which comprises:
    (a) reducing a compound of the Formula (X) to form a compound of the Formula (III):
    (b) reducing the compound of the Formula (III) to form a compound of the Formula (II);
    (c) deprotecting the compound of Formula (II) to form a compound of Formula (I); and
    (c) optionally converting the compound of Formula (I) to a pharmaceutically acceptable salt.
12. A process according to paragraph 9 or paragraph 10, wherein the compound of Formula (X) is obtained by reacting compounds of the Formulae (VII) and (VI) according to paragraph 6.
13. A process according to paragraph 12, wherein the compound of Formula (VII) is obtained by reacting compounds of the Formulae (VIII) and (IX) according to paragraph 4.
14. A process according to paragraph 9 or paragraph 10, wherein the compound of Formula (X) is obtained by reacting compounds of the Formulae (VIII), (IX) and (VI) according to paragraph 8.
15. A process according to any preceding paragraph, which comprises converting the compound of Formula (I) to a salt, e.g. hydrochloride salt.
16. A process according to any preceding paragraph wherein the process is done on a continuous flow, e.g. as a multi-component domino reaction.
17. A process according to any preceding paragraph wherein the compound of the Formula (I) is FTY720.
18. A process for the production of a compound of the Formula (II) or a salt thereof, which comprises reducing a compound of the Formula (III), the Formula (VI) or the Formula (X).
19. A process for the production of a compound of the Formula (III) or a salt thereof, which comprises:
    (a) reacting a compound of the Formula (V) with a compound of the Formula (VI); or
    (b) reducing a compound of the Formula (X).
20. A process for the production of a compound of the Formula (IV) or a salt thereof, which comprises reducing a compound of the Formula (X).
21. A process for the production of a compound of the Formula (V), which comprises reducing a compound of the Formula (VII).
22. A process for the production of a compound of the Formula (X) or a salt thereof, which comprises reacting a compound of the Formula (VII) with a compound of the Formula (VI).
23. A process for the production of a compound of the Formula (X) or a salt thereof, which comprises reacting compounds of the Formulae (VIII), (IX) and (IV).
24. A process for the production of a compound of the Formula (VII) or a salt thereof, which comprises reacting a compound of the Formula (VIII) with a compound of the Formula (IX).
25. A process according to paragraphs 18 to 24 wherein the process is done on a continuous flow, e.g. as a multi-component domino reaction.

In addition the invention relates to following compounds, and the salts thereof, which may be formed during the steps of reduction, for example during the reduction of a compound of formula (X):

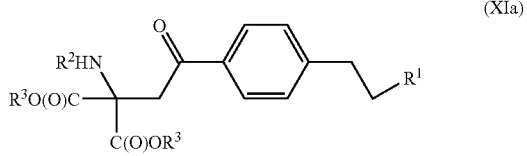

(XIa)

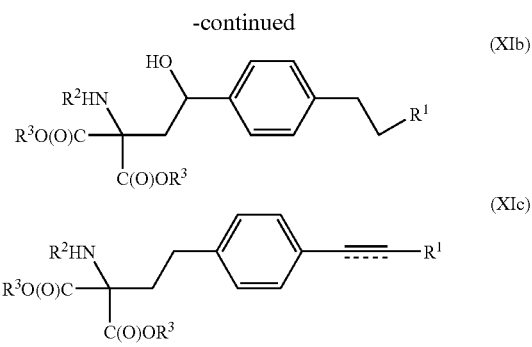

The following processes are also covered by the present invention:
1a. A process for the production of a compound of the formula (XIa) which comprises reducing a compound of formula (X).

The following processes are also covered by the present invention:
1a. A process for the production of a compound of the formula (XIb) which comprises reducing a compound of formula (X).

The following processes are also covered by the present invention:
1a. A process for the production of a compound of the formula (XIc) which comprises reducing a compound of formula (X).

The invention also relates to the use of the various compounds, e.g. selected from compounds of the Formulae (III), (V), (VII), (X), (XIa), (XIb) and (XIc), and their salts, for the production of a 2-amino-2-[2-(4-$C_{2-20}$-alkyl-phenyl)ethyl]propane-1,3-diol, e.g. FTY720, or a pharmaceutically acceptable salt thereof.

The compound of Formula (I) or the intermediate compounds may be purified and/or separated by a conventional manner such as recrystallization, column chromatography, distillation, centrifugal separation, washing or drying.

The compound of Formula (I) may be converted to a pharmaceutically acceptable salt. Examples of salts include salts with inorganic acids, such as hydrochloride, hydrobromide, and sulfate, salts with organic acids, such as acetate, lactate, succinate or tartarate, fumarate, maleate, benzoate, citrate, malate, methanesulfonate and benzenesulfonate salts. A preferred salt is a hydrochloride salt. Compounds of Formula (I), in particular FTY720, may be converted into the hydrochloride salt form in accordance with known methods, e.g. by addition of HCl to the last reaction step or prior to recrystallization.

With regard to each of the various Formulae and processes described herein. $R^1$ may be, for example. $C_{1-18}$ alkyl, wherein the alkyl group may be straight or branched. In an embodiment, $R^1$ is hexyl. In a particular embodiment, $R^1$ is n-hexyl, i.e. the compound of Formula (I) is FTY720.

Suitable protecting groups which may be represented by $R^2$ are described in "Protective Groups in Organic Synthesis", T. W. Greene, J. Wiley & Sons NY (1981), 219-287. Examples include acyl such as formyl, acetyl, benzoyl; alkoxycarbonyl e.g. tert-butyloxycarbonyl; allyloxycarbonyl; trityl; and the like. In an embodiment, $R^2$ is acyl, e.g. acetyl. Acyl groups may be removed using procedures well known in the art. In an embodiment. $R^2$ is an acyl group which is removed using an alkali metal hydroxide, e.g sodium hydroxide, potassium hydroxide or lithium hydroxide.

Each $R^3$ may be independently selected from methyl, ethyl, n-propyl, isopropyl, n-butyl, sec-butyl, isobutyl and tert-butyl.

Examples of leaving groups which may be represented by $R^4$ or $R^6$ include halo, i.e. fluoro, chloro, bromo or iodo. In a particular embodiment, $R^4$ is bromo or chloro.

Examples of leaving groups which may be represented by $R^5$ include halo, i.e. fluoro, chloro, bromo or iodo. In a particular embodiment, $R^5$ is bromo. Other examples include mesylate, besylate, tosylate, nosylate and brosylate groups, which may be obtained by esterification of a hydroxy group with an appropriate sulfonyl halide.

In embodiments, the optional third bond represented by "----" is absent. In other embodiments, the optional third bond represented by "----" is present.

The various intermediate compounds disclosed herein, e.g. compounds of the Formulae (III), (V), (VII), (X), (XIa), (XIb) and (XIc), may also have therapeutic utility. In particular, the intermediate compounds, e.g. compounds of the Formulae (III), (V), (VII)), (X), (XIa), (XIb) and (XIc) may be useful as sphingosine-1 phosphate (S1P) receptor agonists or antagonists, e.g. for:

a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells; and b) treatment and prevention of autoimmune disease or of inflammatory conditions, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis. Graves opthalmopathy, alopecia greata and others, allergic diseases. e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis.

For the above uses the required dosage will of course vary depending on the mode of administration, the particular condition to be treated and the effect desired. In general, satisfactory results are indicated to be obtained at daily dosages of from about 0.1 to about 100 mg/kg body weight. An indicated daily dosage in the larger mammal, e.g. humans, is in the range of from about 0.5 mg to 2000 mg, conveniently administered, for example, in divided doses up to four times a day or in retard form.

The compounds may be administered by any appropriate route, e.g. orally, for example in the form of a tablet or capsule, topically or parenterally, for example intravenously. Pharmaceutical compositions may be manufactured in conventional manner by mixing with the compounds with a pharmaceutically acceptable carrier or diluent. Unit dosage forms for oral administration contain, for example, from about 0.1 mg to about 500 mg of active substance.

The compounds may be administered in free form or in pharmaceutically acceptable salt form, e.g. as indicated above. Such salts may be prepared in conventional manner and exhibit the same order of activity as the free compounds.

The compounds may be administered as the sole active ingredient or together with other drugs in immunomodulating regimens or other anti-inflammatory agents e.g. for the treatment or prevention of allograft acute or chronic rejection or inflammatory or autoimmune disorders. For example, they may be used in combination with calcineurin inhibitors, e.g. cyclosporin A, cyclosporin G, FK-506, ABT-281, ASM 981; an mTOR inhibitor, e.g. rapamycin, 40-O-(2-hydroxy)ethyl-rapamycin. CCI779, ABT578 or AP23573 etc.; corticosteroids; cyclophosphamide; azathioprene; methotrexate; another S1P receptor agonist, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists.

Where a compound is administered in conjunction with another immunomodulating or anti-inflammatory agent, dosages of the co-administered immunomodulating or anti-inflammatory agent will of course vary depending on the type of co-drug employed, on the condition to be treated and so forth.

The present invention thus provides:

1. A method of treating or preventing organ or tissue transplant rejection, comprising administering to a subject a therapeutically effective amount of one or more intermediate compounds, e.g. selected from compounds of the Formulae (III), (V), (VII), (X), (XIa), (XIb) and (XIc), or a pharmaceutically acceptable salt thereof.
2. A method of treating or preventing an autoimmune disease or inflammatory condition, for example multiple sclerosis, comprising administering to a subject a therapeutically effective amount of one or more intermediate compounds, e.g. selected from compounds of the Formulae (III), (V), (VII), (X), (XIa), (XIb) and (XIc), or a pharmaceutically acceptable salt thereof.
3. An intermediate compound, e.g. selected from compounds of the Formulae (III), (V), (VII), (X), (XIa), (XIb) and (XIc), or a pharmaceutically acceptable salt thereof, for use as a pharmaceutical.
4. A pharmaceutical composition comprising one or more intermediate compounds, e.g. selected from compounds of the Formulae (III), (V), (VII), (X), (XIa), (XIb) and (XIc), or a pharmaceutically acceptable salt thereof, and a pharmaceutically acceptable diluent or carrier.
5. Use of one or more intermediate compounds, e.g. selected from compounds of the Formulae (III), (V), (VII), (X), (XIa), (XIb) and (XIc), or a pharmaceutically acceptable salt thereof, for the preparation of a medicament, e.g. in a method as disclosed above.
6. A pharmaceutical combination comprising (a) one or more intermediate compounds, e.g. selected from compounds of the Formulae (III), (V), (VII), (X), (XIa), (XIb) and (XIc), or a pharmaceutically acceptable salt thereof; and (b) a second drug substance, said second drug substance being suitable for the prevention or treatment of a condition described above.
7. A method as defined above comprising co-administration, e.g. concomitantly or in sequence, of (a) one or more intermediate compounds, e.g. selected from compounds of the Formulae (III), (V), (VII), (X), (XIa), (XIb) and (XIc), or a pharmaceutically acceptable salt thereof; and (b) a second drug substance, said second drug substance being suitable for the prevention or treatment of a condition described above.

The invention also provides a composition comprising a compound of Formula (I), e.g. FTY720, or a pharmaceutically acceptable salt thereof in combination with a relatively minor proportion of one or more intermediate compounds, e.g. selected from compounds of Formulae (III), (V), (VII), (X), (XIa), (XIb) and (XIc), or a salt thereof.

The following Examples illustrate the invention.

EXAMPLE 1

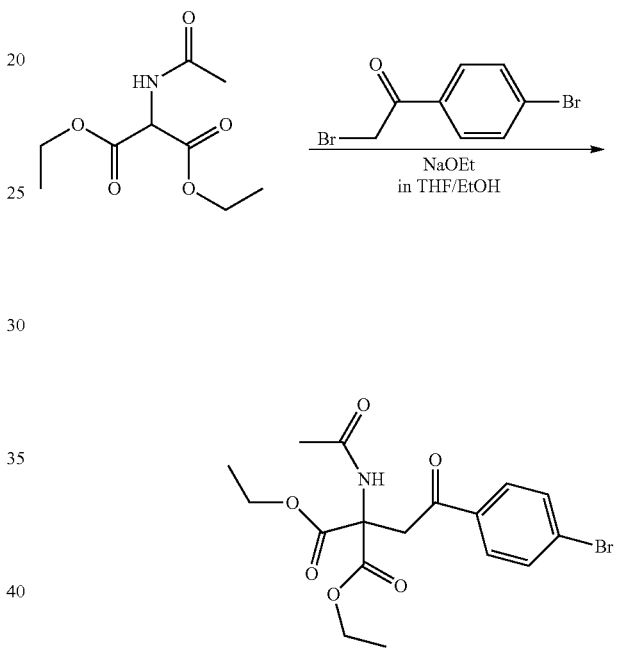

A dry flask is charged with a solution (21% cont.) of sodium ethanolate 1.17 g (0.24 g=3.62 mmol) in ethanol. The solution is diluted with 2 ml of abs. ethanol. Than 1.04 g (4.81 mmol) of diethyl acetamidomalonate is added in portions and is then warmed up to 60° C. for 30 minutes. The clear yellow solution is cooled to room temperature. At room temperature is than added 0.51 g (1.81 mmol) of 4-bromophenacylbromide dissolved in 5 ml of dry ethanol and 2 ml of dry THF via dropping funnel within 10 minutes. HPLC control shows complete conversion of the 4-bromophenacylbromide directly after addition is complete. The reaction mixture is quenched on 10% citric acid (25 ml) at 0° C. under stirring. 50 ml of ethyl acetate is added and the phases are separated. The aqueous phase is extracted three times with 20 ml ethyl acetate. The combined organic phases are then extracted three times with KHCO3 solution and finally dried over $MgSO_4$. After filtration the solvents are evaporated under reduced pressure and finally in high vacuum to give the crude product as a yellow oil. The crude product still contains excess of acetamido malonate which is separated by column chromatography on silica gel (toluene:ethyl acetate=1:1).

$^1$H-NMR: (400 MHz, $CDCl_3$); $_H$ (ppm), δ=1.25 (6H, t, —$CH_3$), 2.00 (3H, s, —$CH_3$ (Ac), 4.22 (2H, s, —$CH_2$—), 4.28 (4H, q, O—CH$_2$—), 7.12 (1H, s, —NHCO), 7.62 (2H, d, arH), 7.84 (2H, d, arH). MS: [M+H]$^+$=415

EXAMPLE 2

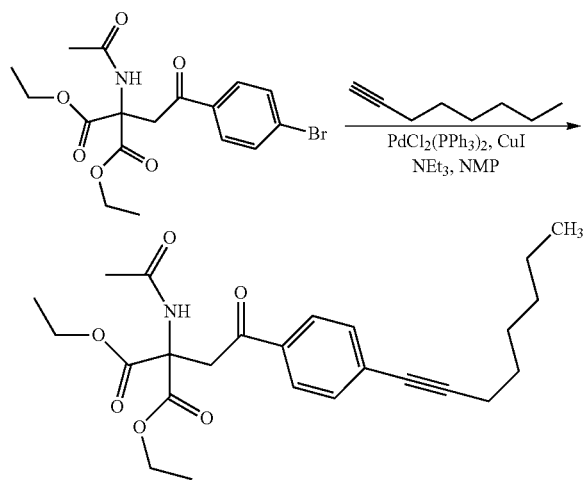

A dried flask is charged under dry nitrogen with 0.83 g (2 mmol) of the compound of Example 1, followed by 9 ml of a mixture NMP (N-methylpyrrolidone) and triethylamine (2:1). To the solution is added under nitrogen 0.33 g (3 mmol) of 1-octyne, 8 mg CuI (~2 mol %), and 21 mg (1.5 mol %) bis(triphenyl-phosphine) palladium(II) chloride. The reaction mixture is stirred at room temperature over night (15 h). HPLC control shows complete conversion. To the orange reaction mixture (suspension) is added 30 ml of water and 30 ml of t-butylmethylether. The biphasic mixture was stirred for 10 min. and then phases are separated. The organic phase is washed 3-times with 20 ml of a citric acid solution (10%) and finally 3-times with 20 ml of brine. The organic phase is dried over MgSO$_4$ filtered and evaporated in vacuum to give a dark colored oil. The crude oil is finally degassed in high vacuum.

$^1$H-NMR: (400 MHz, CDCl$_3$); δ$_H$ (ppm) δ=0.85 (3H, t, —CH$_3$), 1.18 (6H, t, —CH$_3$), 1.20-1.30 (4H, brm, 2x-CH$_2$—), 1.30-1.46 (2H, brm, —CH$_2$), 1.50-1.58 (2H, m, —CH$_2$), 1.90 (3H, s, —CH$_3$ (Ac), 2.35 (3H, t, 2H, proparg.), 4.16 (2H, s, —CH$_2$—), 4.20 (4H, q, 2x-O—CH$_2$—), 7.04 (1H, s, —NH—CO), 7.38 (2H, d, arH), 7.80 (2H, d, arH). MS: [M+H]$^+$=444.3

EXAMPLE 3

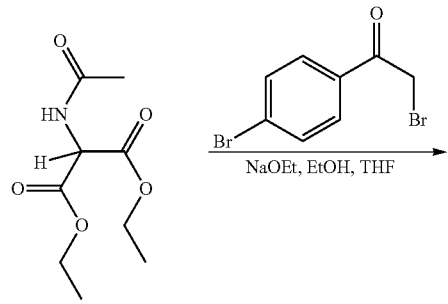

NaOEt, EtOH, THF

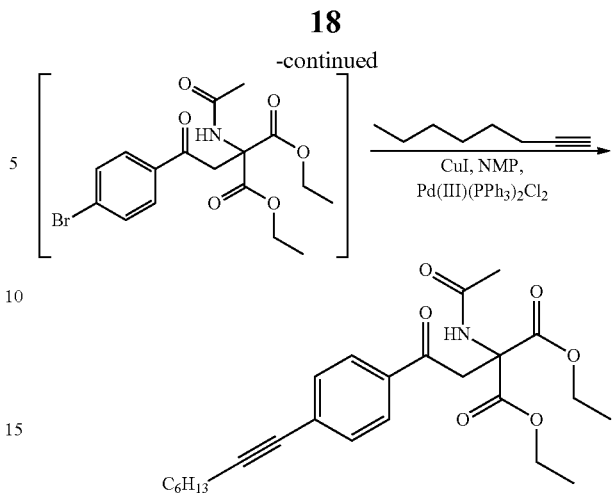

A 50 ml three necked flask, pre-dried under nitrogen atmosphere, is charged with 4.5 g (14 mmol) sodium ethoxide (21% solution in ethanol) and 7.5 ml of additional dry ethanol. Then 4.5 g (21 mmol) of acetamido malonicacid diethylester is added in small portions at room temperature under stirring during 10 minutes. The clear yellow solution is stirred for further 30 min. at 25° C. Then 1.9 g (7 mmol) 4-bromo-phen-acylbromide dissolved in 7 ml of tetrahydrofuran and 23 ml of ethanol is then added via a dropping funnel within 30 min. at 25° C. HPLC control directly after the addition shows complete conversion of the phenacylbromide.

To the solution of alkylated malonat is added 7 ml of dry NMP and 1.54 g (14 mmol) of 1-Octin. Then the catalyst cocktail of 0.047 g (0.25 mmol) copper iodide and 0.197 g (0.28 mmol) bis(triphenylphosphine)-Pd-(II)-chloride is added. Afterwards suspension is heated to 80° C. HPLC-analysis after 30 min. shows conversion of the arylbromide intermediate.

The reaction mixture is evaporated in vacuum. The residue is then dissolved in 60 ml of TBME and extracted with 30 ml of water. The aqueous phase is twice extracted with 30 ml of TBME and the combined organic phases are washed 4-times with 20 ml of water. The organic phase is dried with Na$_2$SO$_4$ and filtered. The filtrate is evaporated in vacuo to give the crude product. The crude product is purified by column chromatographie over silica gel with eluents (ethyl acetate:heptane, 1:2). $^1$H-NMR as in example 2.

EXAMPLE 4

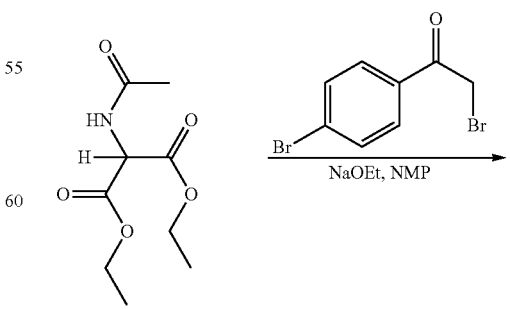

2-Acetylamino-malonic acid diethyl ester

-continued

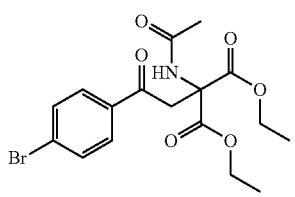

A dry flask is charged under N₂ with 3.25 g of a solution of 21% sodium ethoxide in ethanol (corresponding 10 mmol sodium ethoxide) and 7.5 ml of dry NMP (N-methylpyrrolidinone). Then 3.26 g (15 mmol) solid 2-acetamido malonic acid diethylester is added in portions during 10 minutes leading to a brown suspension. Additional 3.0 ml dry ethanol is added and heated to 43° C. getting a brown-red solution. Now 1.39 g (5 mmol) 4-bromophenacylbromide dissolved in 14 ml NMP is slowly added in 25 minutes via dropping funnel to the deprotonated malonate. HPLC control directly after addition shows conversion of the 4-bromo-phenacylbromid to the desired product.

EXAMPLE 5

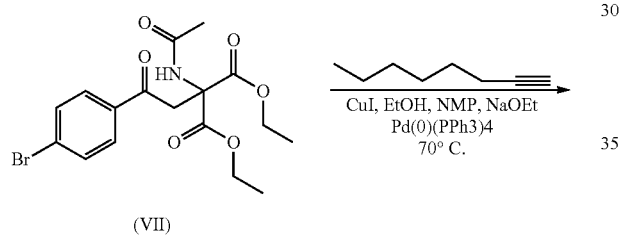

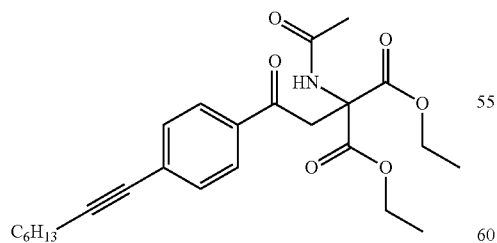

A reaction solution containing 2 mmol of product VII is prepared as described in example 3. The solution is heated up on 65° C. under argon. Then a solution of 0.44 g (4 mmol) 1-octyn, 16 mg (0.07 mmol) copper(I) iodide and 56 mg (0.05 mmol) tetrakis(triphenylphosphine)-Pd-(0) in 2 ml NMP is added. The reaction is heated at 70° C. After 30 min. HPLC control shows already after 25 min.

EXAMPLE 6

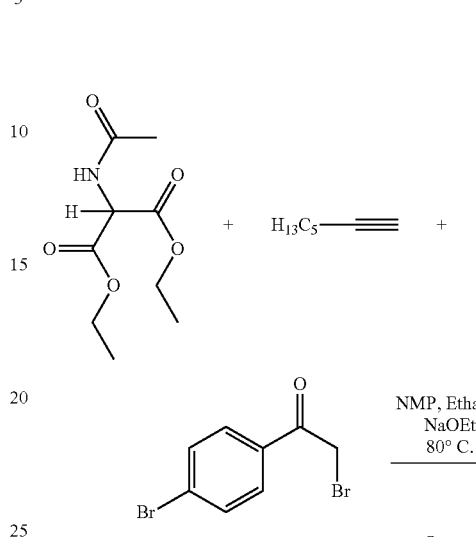

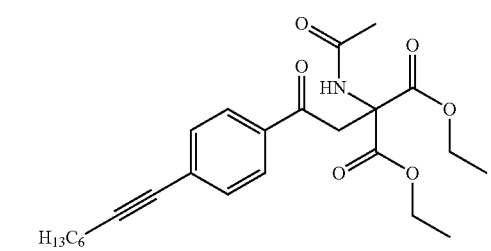

A dry 3-necked flask is charged under dry nitrogen with 3.9 g (12 mmol) sodium ethoxide solution (21% in ethanol), 15 ml ethanol, 3.9 g (18 mmol) 2-acetamido-malonic acid diethylester. To the resulting solution is further added 1.32 g (12 mmol) 1-octyne, 0.04 g (0.2 mmol) copper (I) iodide and 0.17 g (0.24 mmol) bis(triphenyl-phosphine)-Pd-(II)-chloride resulting in a suspension. To this suspension is added 1.7 g (6 mmol) 4-bromo-phenacylbromide dissolved in 8.5 ml NMP and 10 ml of ethanol via a dropping funnel within 30 min. at room temperature. After complete addition the reaction mixture is heated under stirring to 88° C. external temperature (reflux). HPLC control shows after 30 min. conversion to the alkylation product (8.45 min.). The reaction mixture is evaporated in vacuum and worked up and purified as described in Example 3.

EXAMPLE 7

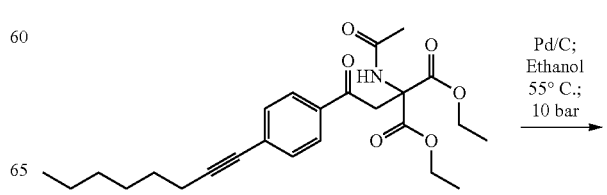

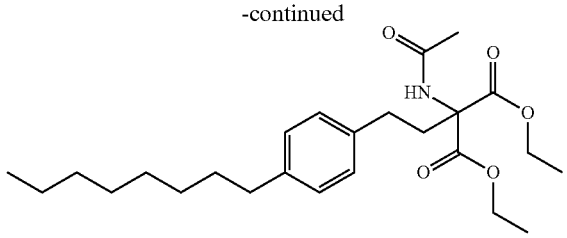

An autoclave is charged with 0.91 g (2 mmol) of starting material from Example 5 and 40 ml of ethanol, and 200 mg of Pd—C, (5%) catalyst (Degussa E-101). The reaction mixture is hydrogenated at a temperature of 55° C. and 10 bar. After 18 h the pressure dropped to 4 bar. HPLC-analysis shows conversion of the starting material to a new intermediate and to the desired product (IV). Further 200 mg of the same catalyst were added and hydrogenation was continued at 4 bar and 55° C.

After further 45 hours HPLC control shows clean conversion to the desired product (IV). The reaction mixture is filtered and washed with ethanol to remove the catalyst. The filtrate is evaporated in vacuum to give a white oil (0.75 g) which crystallized during storage at room temperature. $^1$H-NMR and MS as well as a comparison with an authentic sample proves the structure:

$^1$H NMR: (400 MHz, CDCl$_3$); (ppm) δ=0.85 (3H, t, CH$_2$—C$\underline{H}$$_3$), 1.2-1.35 (16H, m, 6H:O—CH$_2$—C$\underline{H}$$_3$, 10H, C$\underline{H}$$_2$—CH$_2$—CH$_2$—CH$_2$—CH$_2$—CH3), 1.55 (2H, m, C$\underline{H}$$_2$—CH$_2$—Ar), 1.95 (3H, s, C$\underline{H}$$_3$—CO), 2.42 (2H, t, C—C$\underline{H}$$_2$—CH$_2$—Ar), 2.5 (2H, t, C—CH$_2$—C$\underline{H}$$_2$—Ar), 2.68 (2H, t, C$\underline{H}$$_2$—Ar), 4.21 (4H, m, O—C$\underline{H}$$_2$—CH$_3$), 6.75 (1H, s, NH—CO) 7.55 (4H, dd, CH$_{Ar}$) MS: [M+H]$^+$=434

EXAMPLE 8

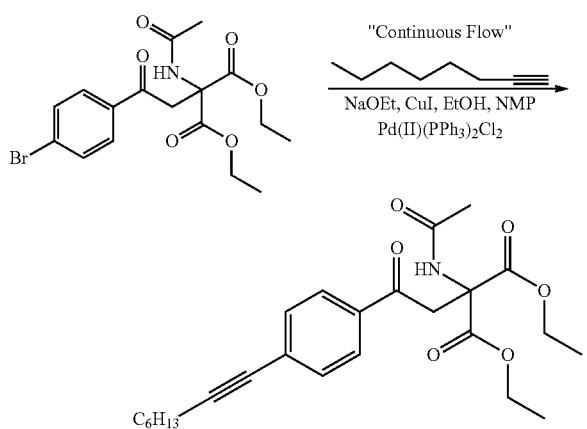

206 g reaction solution with a concentration of 0.17 mmol/g of product VII is prepared as described in the first step in Example 3. A second solution of 0.23 g (1.2 mmol) copper (I)iodide, 0.98 g (1.4 mmol) bis(triphenyl-phosphine)-palladium-(II)-chloride and 7.71 g (69.9 mmol) 1-octyne dissolved in 46.01 g NMP is prepared. The prepared solution has a concentration of 1.26 mmol/g (1-octyne/solution). Both solutions are stored under nitrogen. The Ehrfeld microreactor is purched with dry ethanol and the mäanderreactor is heated up to 110° C. Then the solution with product VII is primed with 0.678 g/min and the 1-octyne-solution with 0.192 g/min. and the system is hold stable at a pressure of 3.5 bar for 45 min and the outgoing reaction solution is collected. The separated reaction-solution is worked up and cleaned as described in Example 3.

The invention claimed is:

1. A process for the production of a compound of the Formula (I) or a pharmaceutically acceptable salt thereof:

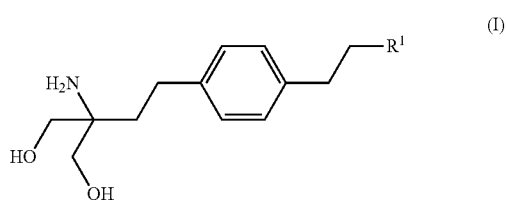

wherein R$^1$ is hydrogen or C$_{1-18}$ alkyl;

which comprises:

(a) reducing a compound of the Formula (X):

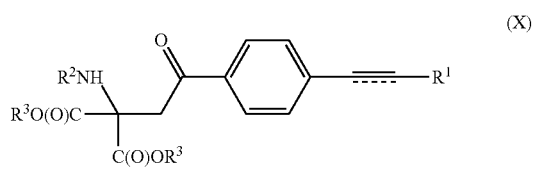

wherein R$^2$ is a protecting group; each R$^3$ is independently C$_{1-4}$ alkyl; and "----" represents an optional third bond;

to form a compound of the Formula (IV):

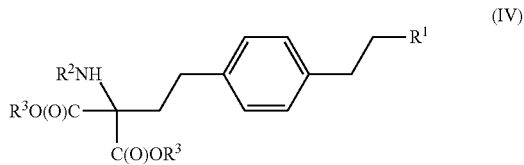

(b) reducing the compound of Formula (IV) to form a compound of the Formula (II):

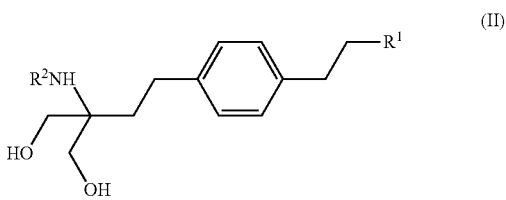

(c) deprotecting the compound of Formula (II) to form a compound of Formula (I); and (d) optionally converting the compound of Formula (I) to a pharmaceutically acceptable salt.

2. A process for the production of a compound of the Formula (I) or a pharmaceutically acceptable salt thereof:

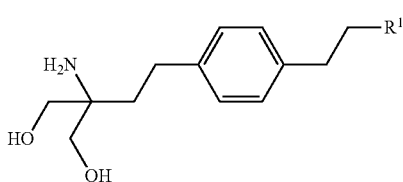

(I)

wherein $R^1$ is hydrogen or $C_{1-18}$ alkyl;
which comprises:
(a) reducing a compound of the Formula (X):

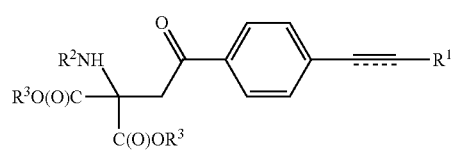

(X)

wherein $R^2$ is a protecting group; each $R^3$ is independently $C_{1-4}$ alkyl; and "----" represents an optional third bond; to form a compound of the Formula (II):

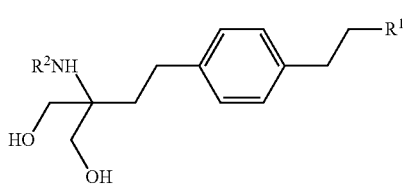

(II)

(b) deprotecting the compound of Formula (II) to form a compound of Formula (I); and
(c) optionally converting the compound of Formula (I) to a pharmaceutically acceptable salt.

3. A process for the production of a compound of the Formula (II) or a salt thereof:

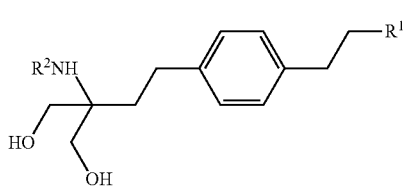

(II)

wherein $R^1$ is hydrogen or $C_{1-18}$ alkyl; and $R^2$ is a protecting group;
which comprises reducing a compound of the Formula (III) or the Formula (X):

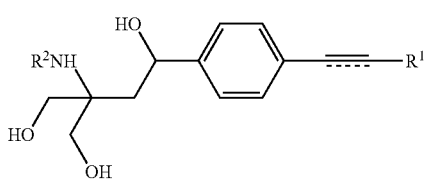

(III)

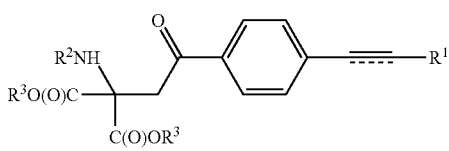

(X)

wherein $R^2$ is a protecting group; each $R^3$ is independently $C_1$ alkyl; and "----" represents an optional third bond.

4. A process for the production of a compound of the Formula (III) or a salt thereof:

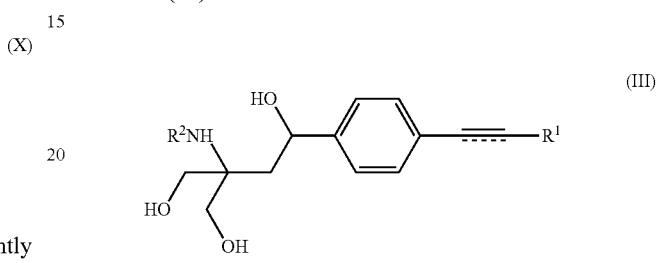

(III)

wherein $R^1$ is hydrogen or $C_{1-18}$ alkyl; $R^2$ is a protecting group; and "----" represents an optional third bond;
which comprises:
(a) reacting a compound of the Formula (V):

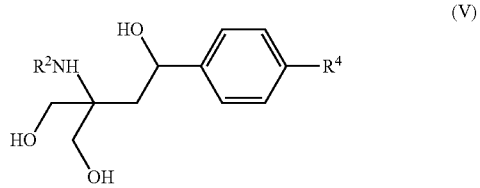

(V)

wherein $R^4$ is a leaving group;
with a compound of the Formula (VI):

$$\equiv\!\!-R^1$$ (VI)

or:
(b) reducing a compound of the Formula (X):

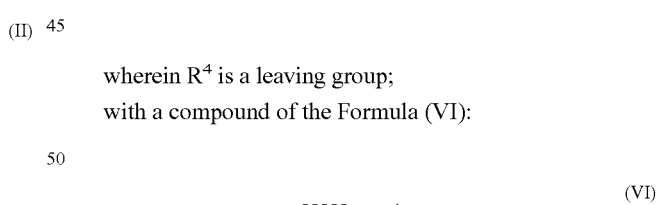

(X)

wherein each $R^3$ is independently $C_1$ alkyl.

5. A process for the production of a compound of the Formula (IV) or a salt thereof:

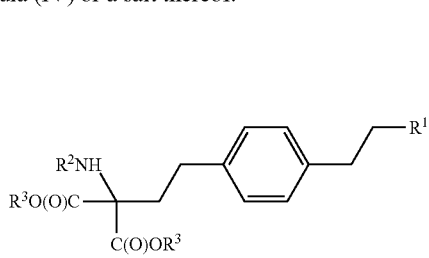
(IV)

wherein $R^1$ is hydrogen or $C_{1-18}$ alkyl; $R^2$ is a protecting group; and each $R^3$ is independently $C_{1-4}$ alkyl;

which comprises reducing a compound of the Formula (X):

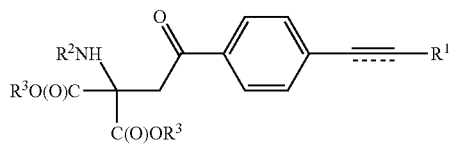
(X)

wherein "----" represents an optional third bond.

6. A process for the production of a compound of the Formula (X) or a salt thereof:

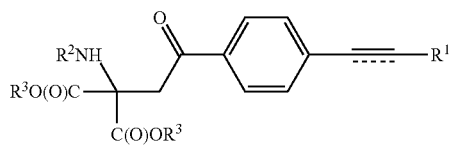
(X)

wherein $R^1$ is hydrogen or $C_{1-18}$ alkyl; $R^2$ is a protecting group;

each $R^3$ is independently $C_{1-4}$ alkyl; and "----" represents an optional third bond;

which comprises reacting a compound of the Formula (VII):

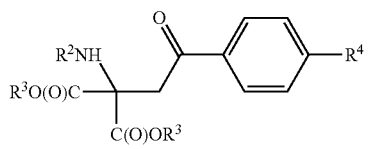
(VII)

with a compound of the Formula (VI):

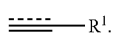
(VI)

7. A process for the production of a compound of the Formula (X) or a salt thereof:

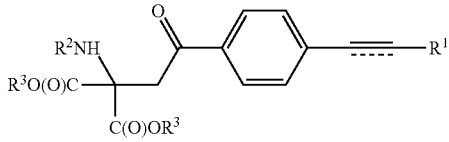
(X)

wherein $R^1$ is hydrogen or $C_{1-18}$ alkyl; $R^2$ is a protecting group; each $R^3$ is independently $C_{1-4}$ alkyl; and "----" represents an optional third bond;

which comprises the steps of:

(a) reacting a compound of the Formula (VIII)

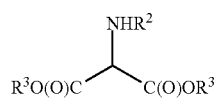
(VIII)

with a compound of the Formula (IX):

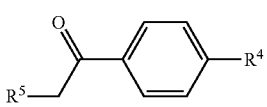
(IX)

wherein each $R^4$ and $R^5$ is a leaving group to obtain a compound of Formula (VII);

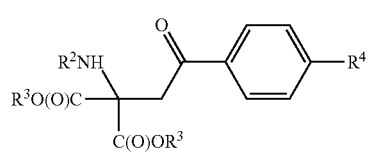
(VII)

(b) reacting a compound of the Formula (VI)

$$\equiv\!\!-\!R^1$$ (VI)

with the compound obtained in step (a) to obtain a compound of Formula (X).

8. The process of claim 1, which is performed on a continuous flow.

9. A compound of one of the following Formulae or a salt thereof:

(V)

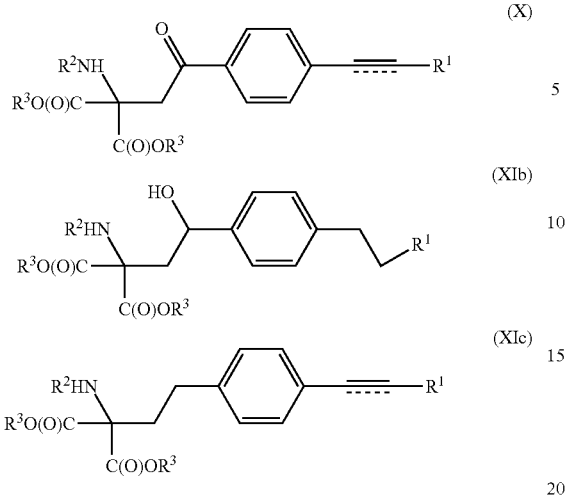
wherein $R^1$ is hydrogen or $C_{1-18}$ alkyl; $R^2$ is a protecting group;
each $R^3$ is independently $C_1$ alkyl;
$R^4$ is a leaving group;
and "----" represents an optional third bond.
* * * * *